United States Patent [19]

Dear et al.

[11] 4,000,188
[45] Dec. 28, 1976

[54] ALKYLTHIOAMIDO SULFONIC ACIDS AND DERIVATIVES THEREOF

[75] Inventors: Robert Ernest Arthur Dear, Mount Kisco; Eduard Karl Kleiner, New York, both of N.Y.

[73] Assignee: Ciba-Geigy Corporation, Ardsley, N.Y.

[22] Filed: Dec. 19, 1975

[21] Appl. No.: 642,270

[52] U.S. Cl. .................. 260/513 N; 260/294.8 F; 260/347.2; 260/429 R; 260/429.9; 260/431; 260/501.15; 260/501.21; 260/503; 260/470; 260/481 R; 260/507 R; 252/526; 252/545; 252/DIG. 11

[51] Int. Cl.² .................. C07C 143/155

[58] Field of Search .................. 260/513 N, 513 F

[56] References Cited

UNITED STATES PATENTS

| | | | |
|---|---|---|---|
| 3,235,549 | 2/1966 | Broussalian | 260/513 N |
| 3,544,597 | 12/1970 | Killam | 260/513 N |
| 3,793,226 | 2/1974 | Danzik | 260/513 N |

*Primary Examiner*—James O. Thomas, Jr.
*Assistant Examiner*—Nicky Chan
*Attorney, Agent, or Firm*—Nestor W. Shust

[57] ABSTRACT

The invention is directed to alkylthio alkylamido sulfonic acids and salts of the formula

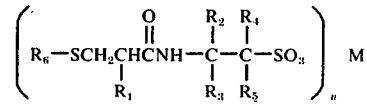

$R_6$ is unsubstituted or substituted alkyl, cycloalkyl or phenyl, alkylthio, tert-alkylamine, furfuryl or a group derived from a polyfunctional mercaptan, $R_1$ is hydrogen or lower alkyl and each of $R_2$, $R_4$ and $R_5$ is individually hydrogen or a hydrocarbon radical. $R_3$ is hydrogen, alkyl, aryl or pyridyl, M is hydrogen, a monovalent alkali metal, an alkaline earth metal, an organic base or ammonium, and $n$ is an integer corresponding to the valency of M. Said compounds are prepared by a base catalyzed addition reaction of a reactive mercaptan to an alkylenylamidoalkane sulfonic acid salt. The compounds are useful as surfactants.

8 Claims, No Drawings

ALKYLTHIOAMIDO SULFONIC ACIDS AND DERIVATIVES THEREOF

DETAILED DISCLOSURE

The present invention is directed to novel alkylthio alkylamido sulfonic acids and salts of the formula

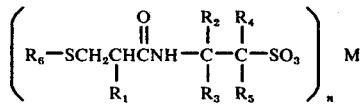

wherein
- $R_1$ is hydrogen or lower alkyl,
- $R_2$, $R_4$ and $R_5$ are independently hydrogen or alkyl group of 1 to 12 carbons,
- $R_3$ is hydrogen, alkyl of 1 to 12 carbons, phenyl, tolyl or pyridyl,
- $R_6$ is a straight or branched chain alkyl or 1 to 25 carbons, substituted alkyl, cycloalkyl of 3 to 8 carbons, alkyl substituted cycloalkyl, or a linking group derived from a di or polyfunctional mercaptan, phenyl or halophenyl, tert-alkylamino or furfuryl, and
- M is hydrogen, a monovalent alkali metal, an alkaline earth metal, an organic base or ammonium, and
- n is an integer corresponding to the valency of M, i.e., 1 or 2.

The alkyl groups of $R_2$, $R_4$ and $R_5$ can be branched or straight chain alkyl of 1 to 18 carbons or cyloalkyl of 3 to 8 carbons. Illustrative examples of such groups are methyl, ethyl, propyl, isopropyl, n-butyl, tert-butyl, n-amyl, tert-amyl, and the various isomers of octyl, decyl and dodecyl, but methyl is preferred. Most preferably $R_4$ and $R_5$ are hydrogen and $R_2$ is methyl.

The group $R_3$ is preferably alkyl and most preferably methyl.

The group $R_1$ is hydrogen or lower alkyl having 1 to 4 carbons, and preferably hydrogen or methyl, and most preferably hydrogen.

The group $R_6$ can be straight or branched chain alkyl of 1 to 25 carbons; or alkyl substituted by groups selected from cyano, hydroxy, alkoxy having 1 to 8 carbons, an ester group derived from a monocarboxylic acid of up to 6 carbons and an alkyl group of 1 to 18 carbons, alkylthio group having 2 to 18 carbons, phenyl and phenyl substituted by halogen especially chlorine, or alkyl having 1 to 18 carbons, a tertiary alkylamine having 1 to 4 carbons or furfuryl; cycloalkyl or cycloalkyl substituted by alkyl of 1 to 4 carbons, or a linking group derived from a di or a polyfunctional mercaptan, said group being selected from a. $Q+CH_2)_{2-6}$
b. $Q+CH_2)_{1\ to\ 4}\ O+CH_2)_{1\ to\ 4}$
c. $Q+CH_2)_{1\ or\ 2}\ COOCH_2CH_2OOC+CH_2)_{1\ or\ 2}$
d. $(R_7)_xC+CH_2OOC+CH_2)_{1\ or\ 2}]_{4-x}$ where $R_7$ is alkyl of 1 to 4 carbons, preferably 1 or 2 carbons, and x is zero, 1 or 2; and (e) 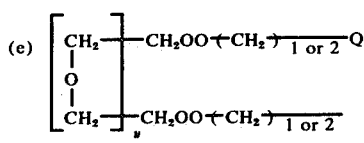

where y is 1 to 14, said Q being the group

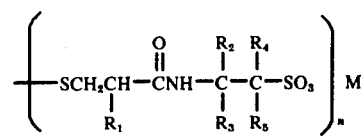

The alkylthioamido sulfonic acids and their salts of this invention can be made by the base catalyzed addition reaction of a reactive mercaptan to an alkenylamidoalkane sulfonic acid salt of the formula

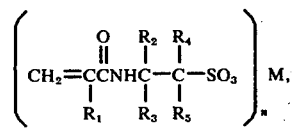

where M is an alkali metal, an alkaline earth metal, a common organic base or ammonium. The alkali metals particularly useful are sodium, potassium and lithium. M can also be an alkaline earth metal, especially magnesium, calcium, barium, zinc, cadmium or mercury. M can also be derived from organic bases such as trialkylaryl ammonium hydroxides such as benzyl trimethylammonium hydroxide or tetraethylammonium hydroxide, tertiary amines

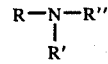

where the R groups are lower alkyl, metal alkoxides, such as sodium methoxide or potassium t-butoxide, aryl or alkyl lithiums such as phenyl lithium, butyl lithium in non-reactive solvents such as tetrahydrofuran, alkali metal amides such as lithium amide or sodium amide and the like. Preferably M is an alkali metal or ammonium, and n is an integer corresponding to the valency of M.

The reactive mercaptan can be any mercaptan that undergoes the condensation reaction with the alkenylamidoalkane sulfonic acid compound. Such mercaptans include alkyl, substituted alkyl and cycloalkyl mercaptans such as straight or branched chain alkylmercaptan of 1 to 25 carbons, 3-mercaptopropionitrile, cyclohexylmercaptan, tricyclodecylmercaptan; mercaptothioethers and mercaptoethers such as 2-mercaptoethylethylsulfide and all the mercaptothioethers in this homologous series up to 18 carbon atoms, that is, 2-mercaptoethyl-n-octadecyl sulfide; furfuryl mercaptan; mercapto esters such as methyl-3-mercaptopropionate and all the mercaptopropionates in the homologous series up to 18 carbons, that is, n-octadecyl-3-mercaptopropionate and thioglycolates such as $HSCH_2COOCH_3$ and homologs up to 18 carbons, that is, $HSCH_2COOC_{18}H_{37}$; aralkylmercaptans such as benzyl mercaptan, p-chlorobenzyl mercaptan and various alkylbenzyl mercaptans such as methylbenzyl mercaptan, ethylbenzyl mercaptan, propylbenzyl mercaptan, hexylbenzyl mercaptan, dodecylbenzyl mercaptan, octadecylbenzyl mercaptan and related homologs; mercaptoalcohols of 2 to 12 carbons such as 2-mercaptoethanol, 3-mercaptopropanol, 6-mercaptohexanol, 8- mercaptooctanol, 12-mercaptododecanol and the like and 1-thioglycerol; mercaptoamines such as 2-diethylaminoethane thiol, diisopropylaminoethane thiol, dimethylaminopropane thiol; di and polyfunctional mercaptans such as 1,2-ethanedithiol, 1,2-propanedithiol, 1,3-propanedithiol, 1,2,3-propanetrithiol, 2,2-dimercapto diethyl ether, glycol dimercapto acetate, glycol dimercapto propionate, pentaerythritol tetra (3-mercaptopropionate), polyethylene glycol dimercapto propionate having 1 to 14 ethylene oxide groups, trimethylolpropane tri(3-mercaptopropionate) and the like.

Alkenylamidoalkane sulfonic acids and their salts are well known in the art and have been thoroughly described, for example, in U.S. Pat. Nos. 2,983,712; 3,332,904; 3,506,707 and British Pat. No. 1,090,779; and German Offenlegungsschift No. 2,105,030. Illustrative examples are listed below:

2-Acrylamidopropanesulfonic acid
2-Acrylamido-2-methylpropanesulfonic acid
2-Methacrylamido-2-methylpropanesulfonic acid
2-Acrylamidobutanesulfonic acid
3-Acrylamidobutane-2-sulfonic acid
3-Acrylamido-2,3-dimethylbutane-2-sulfonic acid
2-Acrylamido-2,4,4-trimethylpentanesulfonic acid
2-Acrylamido-2-phenylethanesulfonic acid
2-Acrylamido-2-phenylpropanesulfonic acid
2-Acrylamido-2-tolylethane sulfonic acid
2-Acrylamido-2-pyridylethane sulfonic acid Especially preferred is 2-acrylamido-2-methylpropanesulfonic acid, available commercially from the Lubrizol Corporation. Using preferred reactants, 1 mole of 2-acrylamido-2-methylpropanesulfonic acid is reacted with one equivalent of a base such as a carbonate, as for example, sodium carbonate, to give an intermediate sodium acrylamido sulfonic acid salt. After carbon dioxide evolution has ceased, a mercaptan dissolved in a solvent such as methanol, is introduced into the reaction mixture. The second step is carried out in the presence of a catalytic amount of a base, such as sodium hydroxide, to yield the product.

The bases used in Steps 1 and 2 may be the same or they may be different. This has no effect on the course of the reaction, but it is generally more convenient and economical to use bases such that M is the same in both steps. Organic bases are generally used when it is desired to obtain a product with increased solubility over those where M is an alkali metal.

The reactions discussed above would normally be carried out in a solvent to facilitate the reaction.

Useful solvents for the reaction are those which will dissolve significant amounts of the alkenylamidosulfonic salt and of the mercaptan. Typical of these are the more polar solvents such as water, methanol, ethanol, isopropanol and dimethylformamide. Other useful solvents are alcohols such as n-propanol, n- and isobutanol, butyl carbitol, ethylene glycol, propylene glycol 1,2 and 1,3, butylene glycol 1,3 and 1,4, 2-methyl-2,4-pentanediol, 2,2-diethyl-1,3-propanediol 1,4-cyclohexanedimethanol (cis and trans) and the like; ethers such as glycol ethers (Dowanols, Carbitols and Cellosolves), ethylene glycol monomethyl ether, ethylene glycol dimethyl ether, ethylene glycol monoethyl ether, ethylene glycol monobutyl ether, diethylene glycol, triethylene glycol, tetraethylene glycol, diethylene glycol monoethyl ether, diethylene glycol monomethyl ether, diethylene glycol diethyl ether, diethylene glycol monobutyl ether, tetrahydrofuran and the like; ketones such as acetone, methyl ethyl ketone, methyl n-propyl ketone, chloroacetone, diacetyl, acetyl acetone, mesityl oxide and the like; N-methyl pyrrolidone, acetonitrile, dioxane and the like.

Step 1 of the reaction is normally carried out at 0° to 25°, although higher or lower temperatures may be employed. Preferably the temperature is controlled at 5°–10° C. This is a simple acid/base neutralization and is thus rapid even at ambient temperatures. Temperatures above about 30° are not recommended since under these circumstances polymerization of the unsaturated amidosulfonic acid may occur. Use of inert gas to blanket the reaction is also useful to prevent unwanted side reactions.

At least a molar equivalent of base is necessary in Step 1 in order that a basic environment will be present in Step 2. Use of an excess of base in Step 1 will not harm the reaction, but large excesses serve no useful purpose and are therefore to be avoided on economic grounds. Step 2 is the base catalyzed addition of a mercaptan to the $\alpha,\beta$-unsaturated sulfonate formed in Step 1. Step 2 may be carried out at temperatures of 0° to 100°, but to achieve reasonable reaction times, a temperature of 50°–80° is preferred. Under these conditions — e.g., in refluxing methanol or ethanol — reaction is complete in 2 to 2½ hours. At 25° the reaction is considerably slower.

The compounds of this invention can be converted to the corresponding sulfones and sulfoxides. This can be accomplished by known oxidation methods, such as reacting the thioether with acetic acid and a peroxide, e.g., $H_2O_2$, as described in greater detail in German OS-DT 2,344,889 which is incorporated herein by reference.

The examples below are presented for illustrative purposes only and do not limit the scope of the invention. The temperature is expressed in ° C.

EXAMPLE 1

Sodium 2-[3-n-Decylthiopropionamido]-2-sulfonate

A 100 ml Morton flask (3 neck) was fitted with a mechanical stirrer, nitrogen inlet, thermometer and an exit vent. 2-Acrylamido-2-methyl-1-propane sulfonic acid (83.63 g; 0.404 mole) was placed in the flask with 175 g water. Anhydrous sodium carbonate (21.84 g; 0.206 mole) was added slowly, resulting in carbon dioxide liberation as the sulfonic acid was neutralized. n-Decyl mercaptan (69.72 g; 0.400 mole) was added to the solution, followed by 175 g isopropanol and benzyltrimethylammonium hydroxide as catalyst (2.09 g of 40% methanol solution; 0.005 mole). The system was heated and stirred at 82° C (reflux temperature) for 12 hours. The contents of the flask were emptied into a large pan and the solvents removed by evaporation at 70° C. The resulting solid was triturated with 1,000 ml acetone, filtered and dried, to give 146.4 g (90.8% of theory) of sodium 2-[3-n-decylthiopropionamido]-2-methylpropane sulfonate as a fine white powder. The structure of the product was confirmed by $H^1$ nmr which showed:

(ppm from tetramethylsilane)
0.85 : 3 protons : $\underline{CH_3}-CH_2-$

-continued

| | | | |
|---|---|---|---|
| 1.25 | : | 16 protons | : $CH_3(\underline{CH_2})_8-CH_2S-$ |
| 1.40 | : | 6 protons | : $-C(\underline{CH_3})_2-$ |
| 2.15–2.75 | : | 6 protons | : $-\underline{CH_2}S\underline{CH_2CH_2}-\overset{O}{\underset{\|\|}{C}}-$ |
| 2.80 | : | 2 protons | : $-\underline{CH_2}SO_3Na$ |
| 8.00 | : | 1 proton | : $-N\underline{H}$ |

EXAMPLE 2

Sodium 2-[-n-Butylthiopropionamido]-2-methylpropane sulfonate

A 500 ml Morton flask (3 neck) was fitted with a mechanical stirrer, nitrogen inlet, thermometer and an exit vent. 2-Acrylamido-2-methyl-1-propane sulfonic acid (52.16 g; 0.252 mole) was placed in the flask with 90 g of water. Anhydrous sodium carbonate (13.46 g; 0.127 mole) was added slowly, resulting in carbon dioxide liberation as the sodium sulfonate was formed. n-Butyl mercaptan (22.55 g; 0.25 mole) was added together with 90 g of isopropanol, followed by benzyltrimethylammonium hydroxide (1.05 g of 40% Methanol solution; 0.0025 mole) as catalyst. The system was heated with stirring for 18 hours at 60° C. The contents of the flask were transferred to a large pan and the solvent was removed by evaporation at 70° C. The resulting paste was triturated with 800 ml dry acetone, filtered and dried, to give 62.7 g (78.6% of theory) of sodium 2-[3-n-butylthiopropionamido]-2-methylpropane sulfonate, as a fine white powder.

EXAMPLES 3 – 5

Following the procedures described in Examples 1 and 2, the following alkylthiopropionamidomethylpropane sulfonates were prepared:

| Ex. | Mercaptan (g) | | USAD* (g) | H$_2$O (g) | i-PrOH (g) | BTMAH* (g) | Prod. (g) |
|---|---|---|---|---|---|---|---|
| 3 | C$_6$H$_{13}$SH | 35.50 | 62.70 | 115 | 115 | 1.67 | 91.9 |
| 4 | C$_8$H$_{17}$SH | 58.52 | 83.63 | 164 | 164 | 1.67 | 141.1 |
| 5 | C$_{12}$H$_{25}$SH | 50.65 | 52.16 | 90 | 90 | 1.05 | 95.4 |

*USAD is unsaturated sulfonic acid derivative, 2-acrylamido-2-methylpropane sulfonic acid.
*BTMAH is benzyl trimethyl ammonium hydroxide.

EXAMPLE 6

Foam tests of the below-shown surfactants of this invention were run according to ASTM-D 1173–53.

Table 1

| | Ross Miles Foam Tests: 0.1% Wt: 25° C | | | |
|---|---|---|---|---|
| | Foam Height (mm) | | | |
| | Deionized Water | | Sea Water | |
| Compound | Initial | 5 Min. | Initial | 5 Min. |
| Example 2 | 20 | 5 | — | — |
| Example 3 | 10 | 0 | 10 | 0 |
| Example 4 | 50 | 5 | 150 | 120 |
| Example 1 | 120 | 50 | 155 | 125 |
| Example 5 | 150 | 100 | 115 | 90 |

The above data shows that at least some of the compounds of this invention possess exceptionally good foaming property in sea water.

EXAMPLE 7

The surfactants can also be conveniently prepared for use in a relatively non-volatile solvent. It is also advantageous to perform the first part of the reaction in the inverse manner to that already described (i.e., addition of the acrylamidomethylpropanesulfonic acid to an aqueous solution of base) in order to prevent polymerization of the unsaturated monomer, which would decrease the amount of desired product. These variations are illustrated in this example:

Sodium 2-[3-n-Octylthiopropionamido]-2-methylpropane sulfonate

The apparatus was as described in Example 1 (except that the 1,000 ml flask was replaced by a 2,000 ml flask). A solution of sodium hydroxide (99.5 g of 50% aqueous; 1.244 mole) was placed in the flask together with 153 g water and cooled to 0° C. 2-Acrylamido-2-methyl-1-propane sulfonic acid (252.5 g; 1.220 mole) was added slowly in solid form, maintaining the temperature below 10° C. Hexylene glycol (2-methyl-2,4-pentanediol; 224.8 g) was added followed by n-octyl mercaptan (175.0 g; 1.196 mole). The pale yellow solution was stirred at 60° C for 18 hours, cooled to 25° C and filtered to obtain complete clarity. The product was a pale yellow viscous solution consisting of: sodium 2-[3-n-octylthiopropionamido]-2-methylpropane sulfonate as a 50% solution in equal parts of water and hexylene glycol (25% each). The yield was 862.9 g solution (95.4% of theory). The completion of the reaction was shown by thin layer chromatography which showed one product spot and complete absence of reactant spots.

Many surfactants are not effective in hard water because they precipitate with heavy metal ions such as calcium. To overcome this deficiency, it is necessary to employ chelating agents. The surfactants of this invention are particularly effective in hard water without the use of chelating agents.

EXAMPLE 8

The calcium compatibility of the mercaptan adducts was determined by adding calcium nitrate to 0.1 wt% solutions of the compounds shown in Table 2 and examining the solutions visually to see where turbidity appears. The calcium tolerances, as ppm CaCO$_3$ are shown below:

Table 2

| Compound of Example | Structure | Max. ppm CaCO$_3$ Tolerated |
|---|---|---|
| 2 | C$_4$H$_9$SCH$_2$CH$_2$CONHC(CH$_3$)$_2$CH$_2$SO$_3$Na | >1,800 |
| 3 | C$_6$H$_{13}$SCH$_2$CH$_2$CONHC(CH$_3$)$_2$CH$_2$SO$_3$Na | >1,800 |

Table 2-continued

| Compound of Example | Structure | Max. ppm CaCO₃ Tolerated |
|---|---|---|
| 4 | $C_8H_{17}SCH_2CH_2CONHC(CH_3)_2CH_2SO_3Na$ | 900 |
| 1 | $C_{10}H_{21}SCH_2CH_2CONHC(CH_3)_2CH_2SO_3Na$ | >1,800 |
| 5 | $C_{12}H_{25}SCH_2CH_2CONHC(CH_3)_2CH_2SO_3Na$ | 45 |
|  | A commercial amine dicarboxylate | 45 |

This example shows the generally excellent calcium compatibility of these compounds compared to a commercial surfactant.

EXAMPLES 9-19

Following the procedure of Example 1, the compounds described in Table 3 are prepared by reacting the appropriate starting materials.

TABLE 3

| Example | $R_1$ | $R_2$ | $R_3$ | $R_4$ | $R_5$ | $R_6$ |
|---|---|---|---|---|---|---|
| 9 | H | CH₃ | CH₃ | H | H | (CN)CH₂CH₂ |
| 10 | H | CH₃ | CH₃ | H | H | C₈H₁₇SCH₂CH₂ |
| 11 | H | CH₃ | CH₃ | CH₃ | CH₃ | C₁₈H₃₇OOCCH₂CH₂ |
| 12 | CH₃ | CH₃ | CH₃ | H | H | p-ClC₆H₄CH₂ |
| 13 | H | CH₃ | CH₂C(CH₃)₃ | H | H | HOCH₂CH₂ |
| 14 | H | H | C₆H₅ | H | H | (CH₃)₂N(CH₂)₃ |
| 15 | H | H | C₅H₄N | H | H | QCH₂CH₂ |
| 16 | H | H | C₆H₄CH₃ | H | H | QCH₂CH₂OCH₂CH₂ |
| 17 | H | CH₃ | CH₃ | H | H | $\left[\begin{array}{c}CH_2\\|\\O\\|\\CH_2\end{array}\right]_n$—CH₂COO(CH₂)₂— CH₂COO(CH₂)₂Q |
| 18 | H | CH₃ | CH₃ | H | H | (bicyclic structure) |
| 19 | H | CH₃ | CH₃ | H | H | (furan-CH₂) |

| Example | Product |
|---|---|
| 9 | (CN)CH₂CH₂S(CH₂)₂CONHC(CH₃)₂CH₂SO₃Na |
| 10 | [C₈H₁₇SCH₂CH₂S(CH₂)₂CONHC(CH₃)₂CH₂SO₃]₂Mg |
| 11 | C₁₈H₃₇OOCCH₂CH₂S(CH₂)₂CONHC(CH₃)₂C(CH₃)₂SO₃K |
| 12 | p-ClC₆H₄CH₂SCH₂CH(CH₃)CONHC(CH₃)₂CH₂SO₃K |
| 13 | HOCH₂CH₂S(CH₂)₂CONHC(CH₃)(CH₂C(CH₃)₃)CH₂SO₃Na |
| 14 | (CH₃)₂N(CH₂)₃S(CH₂)₂CONHCH(C₆H₅)CH₂SO₃K |
| 15 | Q(CH₂)₂S(CH₂)₂CONHCH(C₅H₄N)CH₂SO₃K |
| 16 | Q(CH₂)₂O(CH₂)₂CONHCH(C₆H₄CH₃)CH₂SO₃Na |
| 17 | $\left[\begin{array}{c}CH_2\\|\\O\\|\\CH_2\end{array}\right]$—CH₂COO(CH₂)₂S(CH₂)₂CONHC(CH₃)₂CH₂SO₃Na ; —CH₂COO(CH₂)₂Q |
| 18 | (bicyclic)-S(CH₂)₂CONHC(CH₃)₂CH₂SO₃K |
| 19 | (furan)-CH₂—S(CH₂)₂CONHC(CH₃)₂CH₂SO₃Na | where $Q = \left(SCH_2CHCONHC\overset{R_2}{\underset{R_1}{|}}-\overset{R_4}{\underset{R_3}{|}}C-SO_3\right)_n M$ with $R_5$

What is claimed is:

1. A compound of the formula

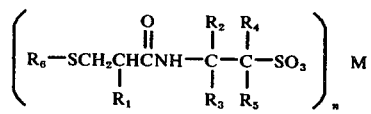

wherein $R_1$ is hydrogen or lower alkyl, $R_2$, $R_4$ and $R_5$ are independently hydrogen or alkyl group of 1 to 12 carbons, $R_3$ is hydrogen or alkyl of 1 to 12 carbons, $R_6$ is a straight or branched chain alkyl of 1 to 25 carbons, and M is hydrogen, a monovalent alkali metal or an alkaline earth metal, and $n$ is an integer corresponding to the valency of M.

2. A compound of claim 1 wherein $R_1$, $R_4$ and $R_5$ are hydrogen, $R_2$ and $R_3$ are methyl, $R_6$ is straight or branched chain alkyl and M is hydrogen, sodium, potassium, or magnesium.

3. A compound of claim 1 which is sodium or potassium 2-[3-n-decylthiopropionamido]-2-methylpropane sulfonate.

4. A compound of claim 1 which is sodium or potassium 2-[3-n-butylthiopropionamido]-2-methylpropane sulfonate.

5. A compound of claim 1 which is sodium or potassium 2-[3-n-hexylthiopropionamido]-2-methylpropane sulfonate.

6. A compound of claim 1 which is sodium or potassium 2-[3-n-octylthiopropionamido]-2-methylpropane sulfonate.

7. A compound of claim 1 which is sodium or potassium 2-[3-n-dodecylthiopropionamido]-2-methylpropane sulfonate.

8. A compound of claim 1 wherein M is hydrogen.

* * * * *